United States Patent

Paumard et al.

[11] Patent Number: 5,118,824
[45] Date of Patent: Jun. 2, 1992

[54] PLATINUM HYDRIDES WITH BRIDGES BIMETALLIC STRUCTURE, METHOD FOR THEIR PREPARATION AND THEIR APPLICATION TO THE CATALYSIS OF CHEMICAL REACTIONS

[75] Inventors: Eric Paumard, Cappel; André Mortreuz, Hem; Francis Petit, Villeneuve-d'Ascq, all of France

[73] Assignee: Atochem, France

[21] Appl. No.: 646,642

[22] PCT Filed: Aug. 9, 1989

[86] PCT No.: PCT/FR89/00416
§ 371 Date: Feb. 6, 1991
§ 102(e) Date: Feb. 6, 1991

[87] PCT Pub. No.: WO90/01486
PCT Pub. Date: Feb. 22, 1990

[30] Foreign Application Priority Data

Aug. 11, 1988 [FR] France ............... 88 10820

[51] Int. Cl.$^5$ .................. C07F 15/00; C07F 9/02
[52] U.S. Cl. ....................... 556/14; 556/16; 556/20; 556/27; 556/28; 556/51; 556/81; 556/110; 556/118; 556/136; 204/59 QM; 568/429
[58] Field of Search ........... 556/136, 137, 14, 16, 556/20, 27, 28, 51, 81, 110, 118; 568/429; 204/59 QM

[56] References Cited

U.S. PATENT DOCUMENTS

| | | | |
|---|---|---|---|
| 3,519,663 | 7/1970 | Obrien et al. | 260/429 |
| 4,522,932 | 6/1985 | Mitchell, III. | 502/153 |
| 4,730,069 | 3/1988 | Kolar et al. | 556/137 |
| 4,797,393 | 2/1989 | Farrell et al. | 556/137 X |

OTHER PUBLICATIONS

Brown et al, *Jrnl. of Organometallic Chemistry*, vol. 236, pp. C33-C36, (1982).

Primary Examiner—Arthur C. Prescott
Attorney, Agent, or Firm—Burns, Doane, Swecker & Mathis

[57] ABSTRACT

The invention relates to platinum hydrides, a process for their preparation and their use as components of catalytic systems. The platinum hydrides have a bridged bimetallic structure represented by the general formula:

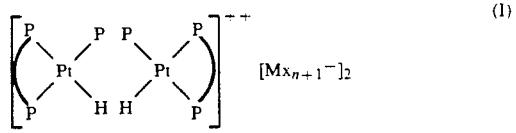

(I)

wherein:
M is a metal of valence n, at least equal to 2,
X is a halogen atom, and
P P is a schematic representation of a ligand of the general formula:

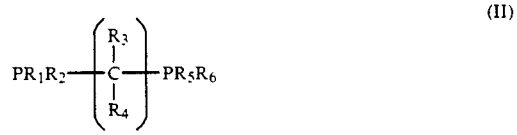

(II)

in which:
$R_1$, $R_2$, $R_5$, and $R_6$, identical or different, are chosen from among aliphatic or cycloaliphatic hydrocarbon radicals with 1 to 8 carbon atoms and aromatic hydrocarbon radicals with 6 to 10 carbon atoms,
$R_3$ and $R_4$, identical or different, are chosen from among a hydrogen atom and aliphatic hydrocarbon radicals with 1 to 8 carbon atoms, possibly functionalized and/or together forming a ring, and
m is an integer higher than or equal to 4.

18 Claims, No Drawings

PLATINUM HYDRIDES WITH BRIDGES BIMETALLIC STRUCTURE, METHOD FOR THEIR PREPARATION AND THEIR APPLICATION TO THE CATALYSIS OF CHEMICAL REACTIONS

The present invention relates to novel platinum hydrides, a process for their preparation and their use as components of catalytic systems intended for the catalysis of chemical reactions, in particular the hydroformylation reactions of ethylenically unsaturated compounds.

A first object of the present invention consists of a novel class of platinum hydrides with a bridged bimetallic structure, represented by the general formula:

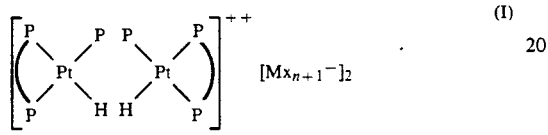 (I)

wherein

M is a metal of valence n, at least equal to 2,

X is a halogen atom, and

P P constitutes a schematic representation of a ligand of the general formula:

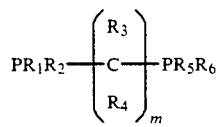 (II)

in which

R1, R2, R5, R6, identical or different, are chosen from among aliphatic or cycloaliphatic hydrocarbon radicals with 1 to 8 carbon atoms and aromatic hydrocarbon radicals with 6 to 10 carbon atoms, R3 and R4, identical or different, are chosen from among a hydrogen atom and aliphatic hydrocarbon radicals with 1 to 8 C atoms, possibly functionalized and/or together forming a ring, and m an integer higher than or equal to 4.

In Formula (I) the platinum hydrides according to the invention, X preferentially is chlorine, n is preferably equal to 2 or 3 and the metal M is preferably chosen from the groups IVB, VIII, IB, IIB, IIIA and IVA of the periodic classification. Even more preferably, M may be chosen from among iron (II), zinc, tin, copper, aluminum and titanium (III).

In the ligand formula (II), it is preferable that $R_1=R_5$ and $R_2=R_6$, and more particularly $R_1=R_2=R_5=R_6$. As examples the following radicals may be cited: methyl, ethyl, isopropyl, tertiobutyl, neopentyl, cyclohexyl, phenyl, etc. If the $R_3$ and $R_4$ are functionalized, they may carry in particular a function such as thiol, alcohol, thioether, amine, imine, acid, ester, amide or ether.

An even more preferred class of ligands is that represented by the general formula:

$$PR_2-CH_2-(CHR')_{n-2}CH_2-PR_2 \quad (III)$$

wherein:

R is chosen from among aliphatic or cycloaliphatic hydrocarbon radicals with 1 to 8 C atoms and aromatic hydrocarbon radicals with 6 to 10 C atoms, R' is chosen from among aliphatic hydrocarbon radicals with 1 to 8 C atoms, possibly functionalized (the function carried being as mentioned above), and m is an integer higher than or equal to 4.

Examples of such ligands are in particular (1S, 2S)(+)trans-1,2-bis(diphenylphosphinometal)cyclohexane, 1,4-bis(diphenylphosphino)-butane and isopropylidene-dihydroxy-2,3-bis-(diphenylphosphino)1,4-butane.

The platinum hydrides according to the invention may be prepared by a number of processes. A first process comprises:

in a first stage the reduction of a solvent containing at least one alkylene carbonate in an electrochemical cell, the anode of which is a metal M, so as to form a chemical combination between the metal M and the alkylene carbonate, then the reaction of said combination with at least one platinum complex of the formula

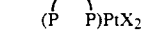

wherein C and

have the abovementioned significance and finally in a last stage the application of a hydrogen atmosphere.

The process therefore comprises, in a first stage, the formation of a chemical combination between the metal M and an alkylene carbonate which may be chosen in particular from among propylene, ethylene, 1,2-butylene and 1,2-hexylene. According to a particular embodiment of the process, the reduction of the solvent may be carried out in the presence of a small quantity of a conducting salt soluble in said solvent, such as for example tetra-n-butylammonium hexafluorophosphate. The presence of this conducting salt makes it possible to advantageously accelerate the reaction of the solvent, in particular at moderate temperatures. The electrochemical reduction phase according to the invention is generally carried out at a temperature between about 10° and 70° C., while maintaining the electrochemical cell under an inert gas atmosphere, such as for example nitrogen, argon or carbon monoxide; it is preferable in view of future uses of the platinum hydrides prepared in this manner, particularly as components of catalytic systems for chemical reactions, that the electrochemical reaction be carried out in the absence of hydrogen. The electrochemical solvent used in this stage of the process necessarily contains at least one alkylene carbonate, such as defined above. It may further contain, in a mixture with the former, another solvent, such as for example an aromatic hydrocarbon (benzene, toluene, xylene, etc.). To carry out the process of the invention it is preferred to use a solvent comprising at least about 10% by volume of the alkylene carbonate.

Within this first process, two variants may be utilized for the electrochemical reduction. According to the first variant, the electrochemical cell contains in addition to the anode of the metal M, a cathode and a reference electrode and the reduction is carried out by charging the cathode to a potential less than or equal to −1.5 Volt relative to the reference electrode and by maintaining this potential for a duration sufficient to assure the production of the desired quantity of the chemical "M-alkylene carbonate" combination; in this case the reference electrode may be for example one of the electrodes Ag/AgCl/Cl⁻, Ag/Ag⁺ and Hg/Hg$_2$Cl$_2$ (calomel). According to the second variant, the electrochemical cell contains a metal M anode and a cathode between which a difference potential higher than or equal to about 10 Volts is maintained, for a duration sufficient to insure the production of the desired quantity of the "M-alkylene carbonate". As in the preceding variant, the metal M anode passes progressively into solution.

As examples of cathodes that may be used in the first process, on the one hand graphite cathodes may be cited, and on the other, metallic cathodes inert relative to the solvent, such as platinum or stainless steel.

The first process according to the invention further comprises the reaction of the chemical combination formed between the metal M and the alkylene carbonate, with the platinum complex of the formula

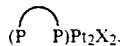(P P)Pt$_2$X$_2$.

This reaction is preferably carried out in at least one solvent of said complex, at a temperature between 10° C. and the boiling temperature of said solvent. Among the solvents of the platinum complex, in particular aromatic hydrocarbons (for example benzene, toluene and the xylenes) and the alkylene carbonates, in particular those, the alkylene compound of which has 2 to 6 C atoms, may be mentioned. The duration of the reaction between the "alkylene carbonate of M" combination and the platinum complex may vary, in keeping with conventional rules well known to those skilled in the art, as a function of the temperature chosen and the concentration of the reactive species in the solvent. As an example, this duration is generally not longer than 20 min, if the reaction temperature is 80° C.

Several modes of carrying out this reaction may be considered within the first process according to the invention. A first mode of embodiment consists of forming an "M-alkylene carbonate" combination by electrochemical reduction, then introducing the platinum complex into the medium in which said combination has been formed, said medium already containing the solvent required for the reaction. A second mode of embodiment consists of forming an "alkylene carbonate-M" combination by electrochemical reduction, separating said combination (in the powder form) from the medium in which it has been formed (for example by filtering, washing and drying the precipitate formed in the electrochemical cell), the introducing said powder into a solution of the platinum complex in the solvent required for the reaction. Finally, a third mode of embodiment consists of forming the "alkylene carbonate-M" combination in the presence of the solvent and the platinum complex, for example by electrochemical reduction; in this case the operation is carried out over a duration sufficient to insure the production of a quantity of electricity at least equal to 0.2 Faraday by gram-atom of platinum. Regardless of the mode of embodiment chosen for the process of the invention, it is desirable that the concentration of the platinum complex in the reaction solvent be between about 0.001 and 0.2 mole per liter.

A second process for the preparation of platinum hydrides according to the invention comprises the reaction of a compound of metal M with a platinum complex of the formula

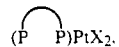(P P)PtX$_2$, in which X and

P P have the significance explained above, in the presence of a solvent containing at least one alkylene carbonate, followed by the application of a hydrogen atmosphere. The metal M compound subjected to this reaction preferably is a compound containing at least one covalent M—O bond, such as an oxide, an alcoholate or a metallic ether.

This second process thus comprises, firstly, a chemical reaction in a solvent medium containing an alkylene carbonate, the alkylene group of which preferably has 2 to 6 carbon atoms, possibly in a mixture with an aromatic hydrocarbon such as benzene, toluene or xylene, preferably, as in the first process of the invention, said medium contains at 10% by volume of the alkylene carbonate. The other reaction conditions, such as temperature and duration, remain the same.

Both in the first and the second process according to the invention, the quantities of "M-alkylene carbonate" and the platinum complex used in the reaction are such that the atomic ratio M/Pt is between about 0.5 and 2 and preferably is equal to 1. In both processes the reaction between the "M-alkylene carbonate" combination and the platinum complex is followed by a hydrogenation stage, i.e. the application of a hydrogen atmosphere; this last stage of the process generally takes place under pressure (up to about 200 bars) and possibly at an elevated temperature (up to 150° C.).

The platinum hydrides according to the invention have a bridged bimetallic structure of Formula (I) verified by the following analytical methods:
nuclear magnetic resonance of phosphorus 31, proton, platinum 195 and the metal M;
infrared spectroscopy establishing the presence of a fine absorption band of the platinum-hydrogen bond at 2010 cm⁻¹;
mass spectrometry.

The platinum hydrides with a bridged bimetallic structure have a remarkable utility as components of catalytic systems for chemical reactions, in particular for the hydroformylation reactions of ethylenically unsaturated compounds. Another object of the present invention therefore consists of the application of these hydrides to the preparation of aldehydes by the hydroformylation of an ethylenically unsaturated organic compound, characterized in that said organic compound is reacted at a temperature between about 10° C. and 300° C. and a pressure of 10 to 350 bars, with a mixture of carbon monoxide and hydrogen in the presence of an effective quantity of said hydride. An effective quantity of the catalytic system is generally such that the molar ratio of the organic compound to the ethylenic insaturation on the platinum is between 100 and 10,000. The molar ratio CO/H$_2$ in the mixture of carbon monoxide and hydrogen in the hydroformylation reaction according to the invention generally is between about 0.5 and 2.

Among the ethylenically unsaturated organic compounds that may be subjected to the hydroformylation reaction according to the invention, the following may be cited:

olefins with 2 to 12 C atoms, such as in particular propylene, 1-butene, 1-hexene, 1-4-methyl-1-pentene, 1-octene, etc., vinylaromatic compounds such as styrene, alphamethylstyrene, dienes, such as for example 4-vinyl-cyclohexane.

The duration of the hydroformylation reaction according to the invention is generally between about 0.5 and 30 h, depending on temperature and pressure.

The hydroformylation process according to the invention makes it possible to obtain, with an excellent conversion proportion, a mixture of normal and branched aldehydes, in which the proportion of normal aldehydes is especially high.

The following examples illustrate the invention without limiting it.

EXAMPLE 1

Into a glass electrochemical cell, the following are introduced under nitrogen: 64 mg of the LPtCl$_2$ compound, the ligand being isopropylene-2,3-dihydroxybis(diphenylphosphino)-1,4-butane, then the solvent consisting of a mixture of 15 cm$^3$ benzene and 10 cm$^3$ propylene carbonate. Following the complete dissolution of the complex, the cathode (consisting of a platinum basket) and the anode (consisting of a tin cylinder) are immersed, then the reference electrode (Ag-/AgCl/N(C$_4$H$_9$)$_4$Cl 0.1M in propylene carbonate) are immersed in the solvent. The temperature is 20° C., the reduction potential is set at $-1.85$ Volt between the cathode and the reference electrode, and the electroreduction is arrested when the quantity of the current having passed the circuit corresponding to an atomic Sn/Pt ratio is equal to 1. During the coulometry, the solution changes from colorless to maroon, while passing through yellow. The solution is then transferred to a previously degassed, 50 cm$^3$ reaction autoclave. The reactor is then charged with hydrogen and to a pressure of 100 bars, then heated to a temperature of up to 100° C. and the agitation started. After about 2 h, the autoclave is cooled and the gaseous mixture eliminated. The solution is transferred to a Schlenk tube and stored under argon.

The compound prepared has been analyzed by the following spectroscopic methods:

nuclear magnetic resonance of phosphorus 31 at 162 MHz with reference to phosphoric acid, making it possible to observe chemical displacements at 4.22 ppm, 8.15 ppm and 13.8 ppm, nuclear magnetic resonance of the proton at 400 MHz relative to tetramethylsulfide, making it possible to observe a chemical displacement at $-5.15$ ppm, nuclear magnetic resonance of platinum 195 at 87 MHz with reference to H$_2$PtCl$_6$ to observe a chemical displacement at $-5390$ ppm, nuclear magnetic resonance of tin 119 at 149 MHz with reference to tetramethyltin showing a chemical displacement at 36 ppm, mass spectrometry establishing that the compound prepared, with a total weight of 2337 g, responds to the following detail formula:

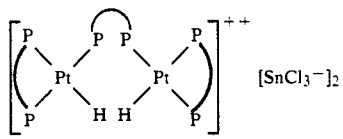

in which P P designates isopropylidene-2,3-dihydroxybis(diphenylphosphino)-1,4-butane. In keeping with the international nomenclature this compound is designated dihydrido[μ-(2,2-dimethyl-1,3-dioxolane-4,5-diyl)bis(-methylene)bis[diphenyl phosphine]-P: P']] bis [[2,2-dimethyl-1,3-dioxolane-4,5-dyl)-bis(methylene) bis[-diphenyl phosphine]-P: P']] diplatinum (II) bis trichlorostannate, and may be diagrammed as follows:

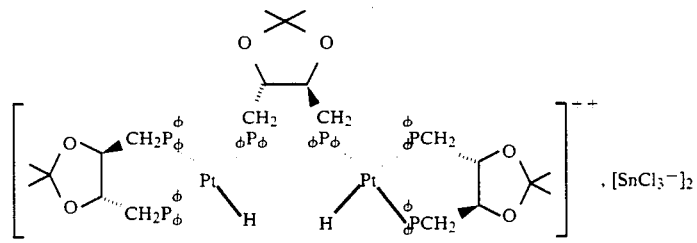

EXAMPLE 2

The platinum hydride solution prepared according to Example 1 is introduced into a stainless steel, 100 cm$^3$ autoclave reactor, equipped with a magnetic bar agitator and styrene is added in a quantity such that the molar styrene/Pt ratio be equal to 100. The reactor is heated to 80° C. and the synthesis gas consisting of an equimolar mixture of carbon monoxide and hydrogen introduced. Finally, the mixture is agitated and the reaction continued at 80° C. under a pressure of 50 bars for 24 h. A mixture is obtained, with a conversion proportion TT (expressed in %), of ethylbenzene, 2-phenyl-2-propanal and 3-phenyl propanal. Analysis of the mixture determined on the one hand the proportion by weight of ethylbenzene EB (expressed in %) and on the other, the molar ratio n/b of normal aldehyde to branched aldehyde. Table I compiles the results obtained.

EXAMPLE 3

The operating process of Example 2 is repeated, with the following exceptions: the reaction is carried out at 90° C. under a pressure of 100 bars for 8 h. Results are given in Table I.

EXAMPLE 4

The process of Example 1 is repeated with the exception that the solvent consists of a mixture of 10 cm³ benzene and 15 cm³ propylene carbonate. The platinum hydride solution obtained in this manner is then used in the hydroformylation of styrene under the operating conditions of Example 2. Results are contained in Table I.

EXAMPLES 5–9

The process of Example 1 is repeated with the exception of the nature of the anode, in which tin is replaced by another metal indicated in Table I. Spectroscopic analyses carried out as in Example 1 indicate that the product formed is a platinum hydride with a bridged bimetallic structure according to Formula (I). The hydroformylation of styrene is then effected according to the operating process of Example 3 with the exception of the duration of the reaction, which is from 8 to 19 h. Results obtained are in Table I.

TABLE I

| example | anode | TT  | EB   | n/b |
| ------- | ----- | --- | ---- | --- |
| 2       | Sn    | 67  | 6    | 4.3 |
| 3       | Sn    | 100 | 8    | 4.0 |
| 4       | Sn    | 53  | 4    | 5.5 |
| 5       | Al    | 90  | 17   | 1.9 |
| 6       | Ti    | 80  | 14.5 | 2.5 |
| 7       | Fe    | 100 | 3    | 5.0 |
| 8       | Cu    | 45  | 18   | 4.8 |
| 9       | Zn    | 100 | 4    | 5.3 |
| 10      | Fe    | 100 | 3    | 9.3 |
| 11      | Fe    | 100 | 15.5 | 8.1 |

EXAMPLE 10

The process of the preparation of platinum hydride of Example 7 (iron anode) is repeated with the exception that the solvent consists of 25 cm³ of a mixture with 75% by volume of benzene. The hydroformylation of styrene is then carried out according to the operating process of Example 3 with the exception of the duration of the reaction, which is 8 to 24 h. Results are listed in Table I.

EXAMPLE 11

Example 10 is repeated with the exception of the hydroformylation reaction, which is effected at 110° C. for 21 h. Result are listed in Table I.

EXAMPLE 12 to 16

64 mg of the LPtCl₂, the ligand consisting of isopropylene-2,3-dihydroxy-bis(diphenylphosphino)-1,4 butane, are reacted in 25 cm³ of a solvent mixture containing 75% by volume benzene and 25% by volume of propylene carbonate, with an iron compound (formula given in Table II) in a quantity such that the atomic ratio Fe/Pt is equal to 1. The reaction mixture is then contacted in an autoclave reactor with hydrogen under a pressure of 100 bars and at a temperature of 100° C. for 2 h. After this, the autoclave is cooled and the gaseous mixture eliminated. The solution is transferred into a Schlenk tube and stored under argon. Spectroscopic analyses carried out as in Example 1 indicate that the product formed is a platinum hydride with a bridged bimetallic structure according to Formula (I), the combining anion being FeCl₃.

Each platinum hydride solution is then used in the hydroformylation of styrene by the process of Example 2, with the following exceptions: the reaction is carried out at 90° C. under a pressure of 100 bars over 24 h (18 h only for Example 13). Results obtained are listed in Table II.

TABLE II

| Example | Iron compound      | TT  | EB  | n/b  |
| ------- | ------------------ | --- | --- | ---- |
| 12      | Fe₂O₃              | 100 | 5.7 | 11.9 |
| 13      | Fe₃O₄              | 100 | 4.8 | 13.2 |
| 14      | Fe(OH)(OCOCH₃)₂    | 92  | 2.5 | 6.0  |
| 15      | Fe(OCOCH₃)₂        | 97  | 2.5 | 9.8  |
| 16      | Fe(OCH₃)₂          | 100 | 4.0 | 5.6  |

We claim:

1. Platinum hydrides with a bridged bimetallic structure, represented by the general formula:

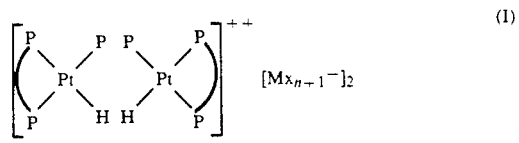

wherein
- M is a metal of valence n, at least equal to 2,
- X is a halogen atom, and
- P P constitutes a schematic representation of a ligand of the general formula:

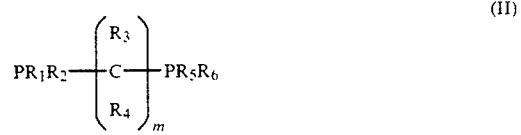

in which
- R1, R2, R5, R6, identical or different, are chosen from among aliphatic or cycloaliphatic hydrocarbon radicals with 1 to 8 carbon atoms and aromatic hydrocarbon radicals with 6 to 10 carbon atoms,
- R3 and R4, identical or different, are chosen from among a hydrogen atom and aliphatic hydrocarbon radicals with 1 to 8 C atoms, possibly functionalized and/or together forming a ring, and
- m an integer higher than or equal to 4.

2. Platinum hydrides according to claim 1, characterized in that X is chlorine.

3. Platinum hydrides according to one of the preceding claims, characterized in that the metal M is chosen from the groups IVB, VIII, IB, IIB, IIIA and IVA of the periodic classification.

4. Platinum hydrides according to one of the preceding claims, characterized in that the metal M is chosen from among iron (II), zinc, tin, copper, aluminum and titanium (III).

5. Platinum hydrides according to one of the preceding claims, characterized in that the ligand

is isopropylene-2,3-dihydroxy-bis(diphenylphosphino)-1,4-butane.

6. Process for the preparation of platinum hydrides according to claim 1, characterized in that it comprises:
in a first stage, the reduction of a solvent containing at least one alkylene carbonate in an electrochemical cell, the anode whereof is made of the metal M, so as to form a chemical combination between the metal M and the alkylene carbonate, then the reaction of said combination with at least one platinum complex of the formula

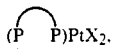

and finally in a last stage, the application of a hydrogen atmosphere.

7. Preparation process according to claim 6, characterized in that the alkylene group of the alkylene carbonate contains 2 to 6 C atoms.

8. Process according to one of claims 6 and 7, characterized in that the reduction of the solvent is carried out in the presence of a small quantity of a conducting salt soluble in the solvent.

9. Process according to one of claims 6 to 8, characterized in that the reduction of the solvent is carried out at a temperature between 10° and 70° C., while maintaining the electrochemical cell under an inert gas atmosphere.

10. Process according to one of claims 6 to 9, characterized in that the solvent further contains an aromatic hydrocarbon in a mixture with the alkylene carbonate.

11. Process according to claim 10, characterized in that said solvent contains at least 10% by volume alkylene carbonate.

12. Process according to one of claims 6 to 11, characterized in that the electrochemical cell contains, in addition to the metal M anode, a cathode and a reference electrode, in that the reduction is carried out by charging the cathode to a potential less than or equal to −1.5 Volt relative to the reference electrode, and that said potential is applied for a duration sufficient to insure the production of the quantity desired of the chemical "M-alkylene carbonate" combination.

13. Preparation process according to one of claims 6 to 11, characterized in that the electrochemical cell contains an anode of metal M and a cathode between which a potential difference higher than or equal to 10 Volts is applied for a duration sufficient to insure the production of the quantity desired of said chemical "M-alkylene carbonate" combination.

14. Preparation process according to one of claims 6 to 13, characterized in that the reaction of the chemical "M-alkylene carbonate" combination and the platinum complex is carried out in a solvent, with the concentration of platinum complex in said solvent being between 0.001 and 0.2 mole per liter.

15. Process for the preparation of platinum hydride according to claim 1, characterized in that it comprises the reaction of a compound of metal M with a platinum complex of formula

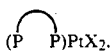

in the presence of a solvent containing at least one alkylene carbonate, followed by the application of a hydrogen atmosphere.

16. Preparation process according to claim 15, characterized in that the metal M compound contains at least one covalent M—O bond.

17. Application of a platinum hydride according to claim 1 as a component of a catalytic system to catalyze a chemical reaction.

18. Application according to claim 17 to the preparation of aldehydes by the hydroformylation of an ethylenically unsaturated organic compound.

* * * * *